United States Patent
Buchanan

Patent Number: 6,053,735
Date of Patent: Apr. 25, 2000

[54] ROOT CANAL PREPARATION METHOD

[76] Inventor: L. Stephen Buchanan, 2335 Foothill La., Santa Barbara, Calif. 93105

[21] Appl. No.: 09/220,725

[22] Filed: Dec. 24, 1998

Related U.S. Application Data

[60] Provisional application No. 60/070,085, Dec. 31, 1997.

[51] Int. Cl.$^7$ ................................................. A61C 5/02
[52] U.S. Cl. ............................................. 433/224; 433/102
[58] Field of Search ..................................... 433/102, 224

[56] References Cited

U.S. PATENT DOCUMENTS

| | | |
|---|---|---|
| 3,863,345 | 2/1975 | Malmin . |
| 3,949,479 | 4/1976 | Malmin . |
| 5,017,138 | 5/1991 | Schilder ................................. 433/102 |
| 5,257,934 | 11/1993 | Cossellu ................................ 433/102 |
| 5,658,145 | 8/1997 | Maillefer et al. ...................... 433/102 |
| 5,735,690 | 4/1998 | Malentacca ........................... 433/102 |
| 5,746,597 | 5/1998 | Maillefer et al. ...................... 433/102 |
| 5,752,825 | 5/1998 | Buchanan . |
| 5,836,764 | 11/1998 | Buchanan . |
| 5,842,861 | 12/1998 | Buchanan . |
| 5,897,316 | 4/1999 | Buchanan . |

OTHER PUBLICATIONS

The Files of Greater Taper: Report from the Trenches, Denistry Today, Sep. 1997 (five pages).

*Primary Examiner*—Nicholas D. Lucchesi
*Attorney, Agent, or Firm*—Henry M. Bissell

[57] ABSTRACT

An improved endodontic procedure for preparation of root canals in teeth comprising the use of selected endodontic instruments such as files or burs in a prescribed series of steps. These steps include using a series of successively smaller instruments in a first crown-down procedure, using the instruments in a reverse sequence in a serial step-back procedure, followed by finishing the preparation of the canal with selected instruments in a second crown-down procedure. Conventional root canal files of standard taper or variably-tapered files may be used in the practice of the method.

11 Claims, 7 Drawing Sheets

ROOT CANAL PREPARATION METHOD

CROSS-REFERENCE TO RELATED APPLICATION

This Complete Application is a continuation of Provisional Application Ser. No. 60/070,085, filed Dec. 31, 1997, with claim of priority therefrom.

BACKGROUND OF THE INVENTION

1. Field of the Invention.

The present invention relates generally to endodontic procedures and methods for enlarging and shaping the root canals of teeth in preparation for filling and sealing.

2. Description of the Related Art.

A relatively common but often difficult dental procedure is the cleaning, shaping and filling of the root canal of a patient's tooth. In the performance of a root canal procedure, a hole is first cut in the crown or exposed portion of the tooth, typically either in the biting surface of the tooth, for posterior teeth, or in the side of the tooth on the interior of the jaw for incisor teeth. Small endodontic instruments known generally as root canal files are then used to clean out the material present in the root canal, and to impart a tapered shape to the root canal so that filling material may be fully inserted into the root canal to thoroughly seal it.

For a great many years, the preparation of root canals has been achieved with the use of files of standard taper. Conventionally when a root canal is being cleaned and shaped, a series of files having increasing diameters is used to gradually enlarge the root canal. The files are held between the thumb and forefinger of one hand by the dentist. Each file in a set of the known prior art has an identical taper from one end to the other. For example, in a typical K-type file set the taper is 0.32 millimeters on every file over the standard 16 mm length of cutting flutes, or 0.02 mm of taper/mm of flute length. This taper is sometimes referred to as a standard ISO (International Standards Organization) taper. Although these file sets have identical tapers, they come in a number of sizes. The size number characterizing the file is the diameter of the file at the tip in hundredths of a millimeter, and the diameter of the file at the large end is thus 0.32 millimeters greater than this tip diameter. A complete set will include sizes 06, 08, 10, 15, 20, 25, 30, 35, 40, 45, 50, 55, 60, 70, 80, 90, 100, 110, 120, 130, and 140, while sizes 08–60 will typically be used. Some manufacturers make certain half-sizes, or off-standard sizes.

Hedstrom-type instruments similarly come in sets of increasing size, typically from 0.10 to 1.40 millimeter tip size, with 0.15–0.60 millimeter tip sizes being most commonly used. Both the K-type and Hedstrom files manufactured to ISO standards, whether twisted or lathe-cut, have flute pitches and frequencies which vary little or none in some sizes (large), but quite a bit in other sizes (small).

One specific procedure for preparing a root canal by using a series of root canal files having decreasing size to clean out the material present in the root canal is known as the "Crown-Down" technique. This technique was developed at the Oregon Health Sciences University Graduate Endodontic Program. It involves proceeding from the top of the tooth, the crown, down toward the root canal terminus employing a series of successively smaller burs and files.

The crown-down technique has been found to be prone to the formation of undesirable apical ledging. Apical ledging occurs when the tip of a file does not follow the curvature of the root canal and instead bores a passage branching out from the root canal. An example is shown in the accompanying FIG. 2A at 24. The occurrence of apical ledging often requires surgical correction.

Schilder in U.S. Pat. No. 5,017,138 describes step-back shaping with multiple recapitulations through a series of instruments, each time from small to large. This technique is referred to as serial step-back shaping. The serial step-back technique is, at best, a difficult and time-consuming method, as the dentist must indirectly gauge the rate of taper in the root canal preparation by the distance interval of step-back of the progressively larger instruments as they fit further back from the canal terminus. Accordingly, a steep learning curve is associated with this technique.

Both of these prior art techniques, crown-down and serial step-back, have attendant disadvantages of requiring numerous repetitive steps (as many as 50 steps) and requiring the use of a large number of instruments (approximately 18) in order to achieve a satisfactory final result. In addition, the skills required to create conservative but adequately tapered shapes in root canals are usually developed only after treating hundreds of clinical cases. Finally, these prior art methods are extremely time-consuming and therefore expensive for the practitioner.

In order to reduce the risk of apical ledging, the initial crown-down technique was modified by the inventor by adding subsequent steps employing a series of successively larger files to step-back from the canal terminus. This modified technique is referred to as the "Crown-Down/Step-Back" technique.

As practiced, both the crown-down and serial step-back procedures generally employ root canal files of fixed taper. In my prior patent application Ser. No. 08/234,290, the disclosure of which is incorporated by reference herein, I disclosed an endodontic treatment system involving variably tapered files and matching variably tapered auxiliary implements and preparation materials which present substantial advantages over the standard fixed taper files.

SUMMARY OF THE INVENTION

In response to the disadvantages inherent in known prior art methods, I have developed the crown-down/step-back/crown-down method of the present invention. One particular method in accordance with my invention involves the steps of initial negotiation and crown-down shaping in a first shaping wave. This is followed by apical step-back preparation in a second shaping wave and concludes with crown-down shaping as a third shaping wave. An optional last step involves post-shape cleaning. In each of the steps during the succeeding shaping waves, appropriate file selection is performed according to the anatomy of the root and root canal being prepared.

The crown-down/step-back/crown-down method of my invention is usually appropriate for canals in small roots. However, the technique is often completed more rapidly in large unoccluded canals. In marked contrast to known prior art methods, the present method requires only between one and eight instruments and can usually be completed in one to four minutes. Although not recommended, it is sometimes possible in the case of large root canals that a single larger taper file can cut the full shape of the canal with just a single instrument.

The disadvantages and limitations of the background art are overcome by the present invention. The present invention differs significantly and advantageously from the root canal cleaning and shaping technology discussed above in numerous respects.

Instead of indirectly creating a tapering canal preparation with the difficult-to-learn, difficult-to-practice and time-consuming serial step-back shaping technique widely used in the profession, the present invention allows full root canal shaping to be accomplished with a reduced number of instruments in substantially less time.

In the practice of the method of the present invention, an initial negotiation step involves the introduction of small files to the end of a root canal system and removal of all pulp remnants prior to crown-down shaping. Following the initial negotiation step, different files of choice may be used including conventional K-files, greater taper files (ranging from 0.06 to 0.12 taper), 0.04 taper ProFiles (a registered trademark of Dentsply/Tulsa Dental, Inc.) and even a Gates-Glidden bur for opening the canal at the orifice level. In the selection of GT™ files of greater taper, files are chosen to match canal size and curvature. For example, a 0.06 file is chosen for extremely thin and/or curved roots. A 0.08 file is chosen for lower anteriors, multi-rooted pre-molars, mesial roots of lower molars and buccal roots of upper molars. A 0.10 file is selected for palatal roots of upper molars and distal roots of lower molars, single canalled pre-molars, lower canines and upper anteriors. A 0.12 file is used for large canals in large roots.

During the crown-down shaping step, each of the selected variably-tapered files is permitted to cut to its own depth, without being forced. The first crown-down wave of shaping is ideally done with one or more GT™ greater taper files, but may also be accomplished with engine-driven 0.04 taper files.

In the second shaping wave, an apical step-back preparation is achieved with one of several choices of instruments, all with successively lesser tapers to insure that they bind primarily at their tips.

When using GT™ files in the initial crown-down shaping step, the ideal time to begin the step-back apical preparation is after one of the GT™ files has advanced to within 1 to 2 mm of the apical terminus.

Variations of the method described to this point may be adapted so that conventional 0.02 tapered K-files may be used during the apical step-back preparation step as well as the 0.04 taper files previously described.

In the final crown-down shaping step, an appropriate GT™ shaping file is used to extend the canal preparation to the terminus, to insure a consistent taper from that terminus to the coronal extent of preparation taper.

The method of the present invention enables practitioners to consistently and ideally shape 95–98% of the root canals treated. In marked contrast to the approximately 50 steps and approximately 18 instruments, and 12–30 min. of procedural time required for the described prior art method, the present invention requires the use of only one to eight shaping instruments, one to 13 steps, and can usually be performed in one to four minutes.

By enabling the practitioner to achieve satisfactory root canal preparations without the use of Gates-Glidden burs, the risk of root perforations is virtually eliminated. A root perforation occurs when too large a bur or file is advanced too far into a curved root canal, and as a result cuts through the side of the root into the adjacent tissue. An example of a root perforation produced by use of too large a bur improperly placed is shown in FIG. 2B. The occurrence of a root perforation often necessitates the extraction of the tooth. By rendering the use of burs unnecessary, the practice of the present invention greatly increases the ease and safety of preparing root canals.

The recent introduction of my files of taper greater than ISO has made possible the complete shaping and preparation of a root canal using substantially fewer instruments than was previously thought possible. Extensive research and development of files of greater taper, so-called GT™ files (GT is a trademark of Dentsply/Tulsa Dental, Inc. of Tulsa, Okla.) and the methods associated with their use have led to the development and refinement of the methods of the present invention.

In addition to the greatly improved ease and simplicity of shaping root canals afforded by the present invention, these methods provide, for the first time, a pre-defined shape throughout the full length of the root canal. One of the most important advantages provided by pre-defined root canal preparations is the resultant ability to optimize cleaning, irrigating, drying and subsequent filling procedures in root canal systems.

However, applying conventional techniques to the recently introduced files of greater taper resulted, in certain root forms, in practitioners experiencing file breakage in the apical regions of the root canal. The present methods virtually eliminate the risk of canal ledging and file breakage in the apical regions of the root canal.

Simplifying and standardizing the preparation of root canals is one of the objects of the present invention. Another object of the present invention is to enable practitioners to achieve consistently ideal root canal shaping results with less training and experience than are required by conventional methods. As a result, the quality of overall endodontic care is greatly improved.

BRIEF DESCRIPTION OF THE DRAWINGS

A better understanding of the present invention may be realized from a consideration of the following detailed description, taken in conjunction with the accompanying drawings, in which.

DESCRIPTION OF THE PREFERRED EMBODIMENTS

Figure 1B:
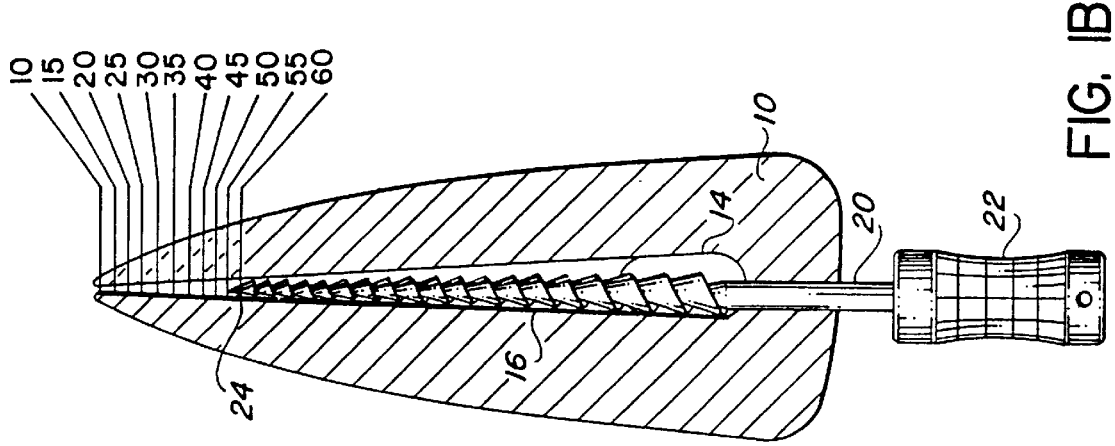
FIG. 1B is a schematic representation indicating the extent of final intrusion of the tips of each of 11 conventional files into the root canal of FIG. 1A, illustrating the conventional step-back technique.
Figure 1A:
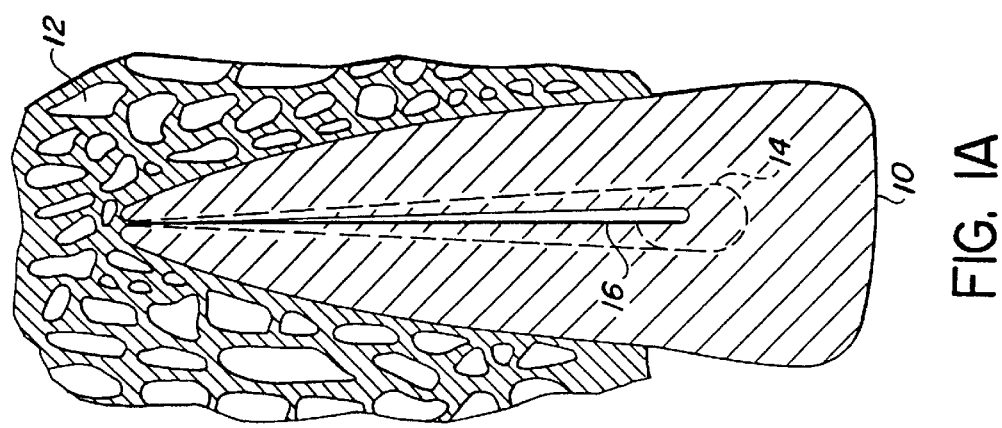
FIG. 1A is a schematic view of a root canal in a tooth, with a portion to be removed during root canal shaping procedures shown in broken lines.

FIG. 1A shows a tooth 10 located in the bone 12 of a jaw. The tooth 10 in FIG. 1A is an incisor, and the opening in the crown of the tooth 10 is cut on the side of the tooth 10 in the interior side of the jaw (not shown), which opening is generally indicated at 14. The tooth 10 has a nerve canal 16 extending to the tip of the tooth 10 which is embedded in the bone 12.

FIG. 1B shows a file 20 inserted into root canal 16, which has been enlarged from the view depicted in FIG. 1A. With conventional files, the step-back prior art technique discussed above is used, with each progressively larger file being inserted shallower and shallower into the root canal 16. The numbers along the root canal 16 near the tip (or apical) end of the root canal 16 represent the maximum extent to which different size files are inserted, with file sizes from 10 to 60 (representing tip diameters from 0.10 mm to 0.60 mm) being used. A minimum of 9 to 11 files are required, with 15 to 17 instruments more frequently being necessary.

Figure 2B:
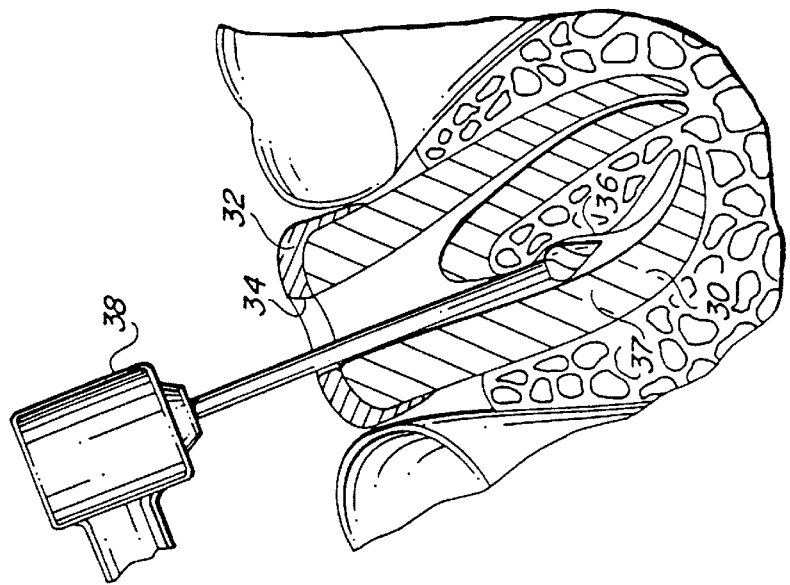
FIG. 2B is a schematic view of a tooth in the process of root canal preparation using a bur in which too large a bur has penetrated too deeply into the root, causing perforation of the root sidewall.
Figure 2A:
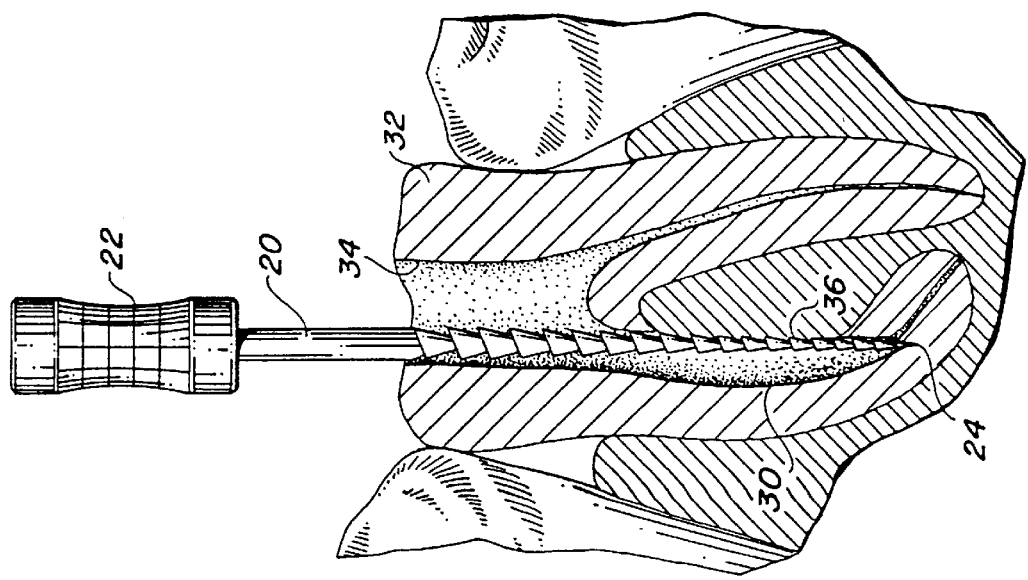
FIG. 2A is a schematic view of a tooth in the process of root canal preparation in which ledging has occurred.

FIG. 2A shows how the conventional wisdom of the prior art crown-down technique teaches directly away from the methods of the present invention. The prior art crown-down technique greatly increases the risk of apical ledging and/or perforation (illustrated in FIGS. 2A and 2B, respectively). The methods of the present invention move in a direction 180° away from the teachings of the prior art. The crown-down/step-back/crown-down method of the present invention enables practitioners to create a pre-defined standardized taper in most root canals without increasing the risk of apical ledging or file breakage in apical canal regions.

Figure 3A:
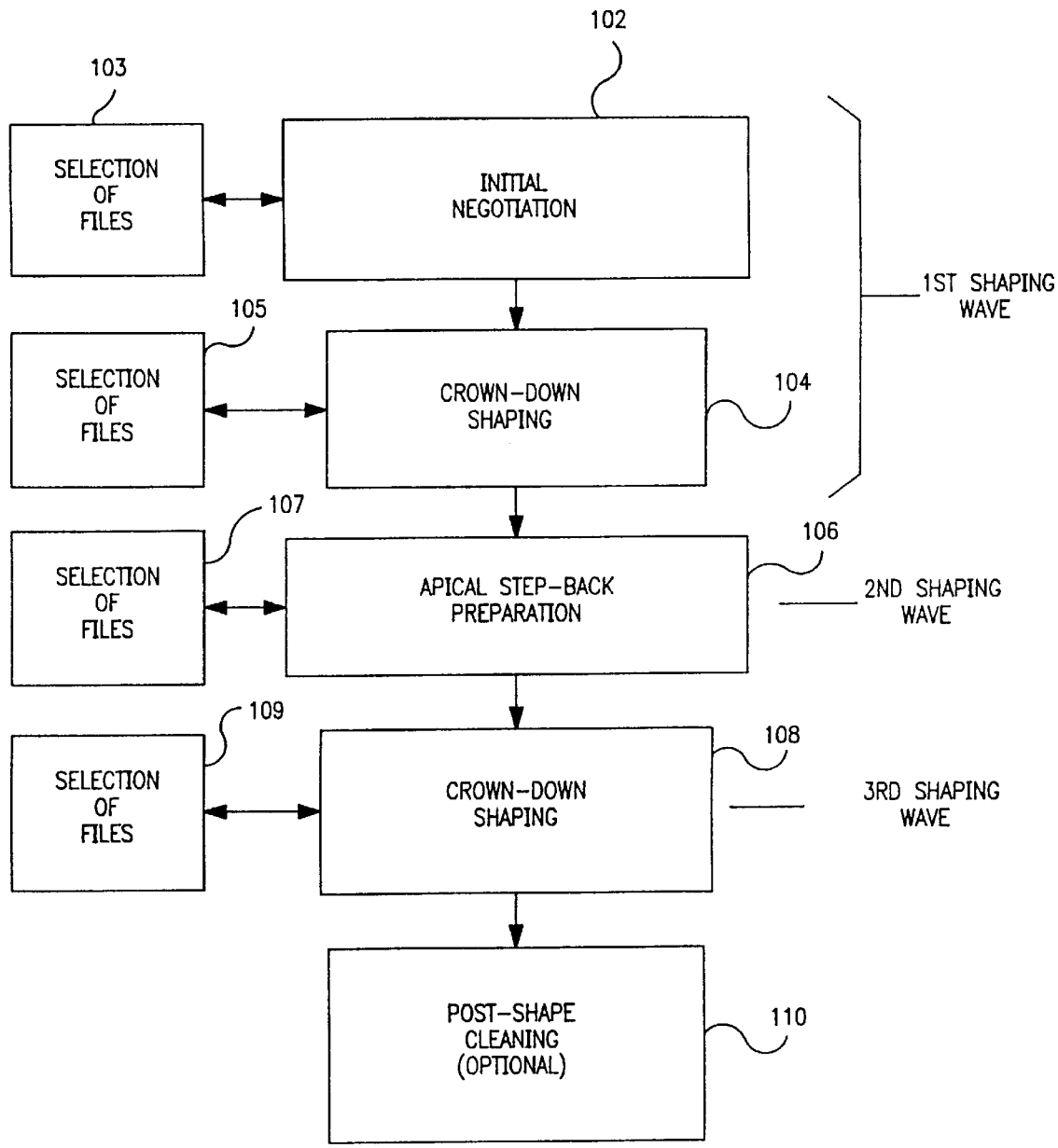
FIG. 3A is a schematic block diagram representing the novel method of my invention.

FIG. 3A is a block diagram illustrating in general the steps of the method of my invention. More detailed procedures with variations of some of the steps are shown in the flowcharts of FIGS. 3B, 4, 5 and 6.

The crown-down/step-back/crown-down method depicted in FIG. 3A involves first, second and third shaping waves corresponding respectively to each of the three major steps. In the first shaping wave, the method 100 includes an initial negotiation step 102 preceding the first crown-down shaping step 104. During the initial negotiation step 102, there is a selection of files, designated 103, to be used in the step 102. Another selection of files, designated 105, is associated with the initial crown-down shaping step 104.

In the second shaping wave, the apical step-back preparation step 106 is performed, again with a selection of files, designated 107, for performing the step-back preparation. In the third shaping wave the second crown-down shaping step 108 is performed in which there is again a selection of files, designated 109. Finally, if appropriate, the post-shape cleaning is performed in accordance with the instructions for practicing the method 100.

Figure 3B:
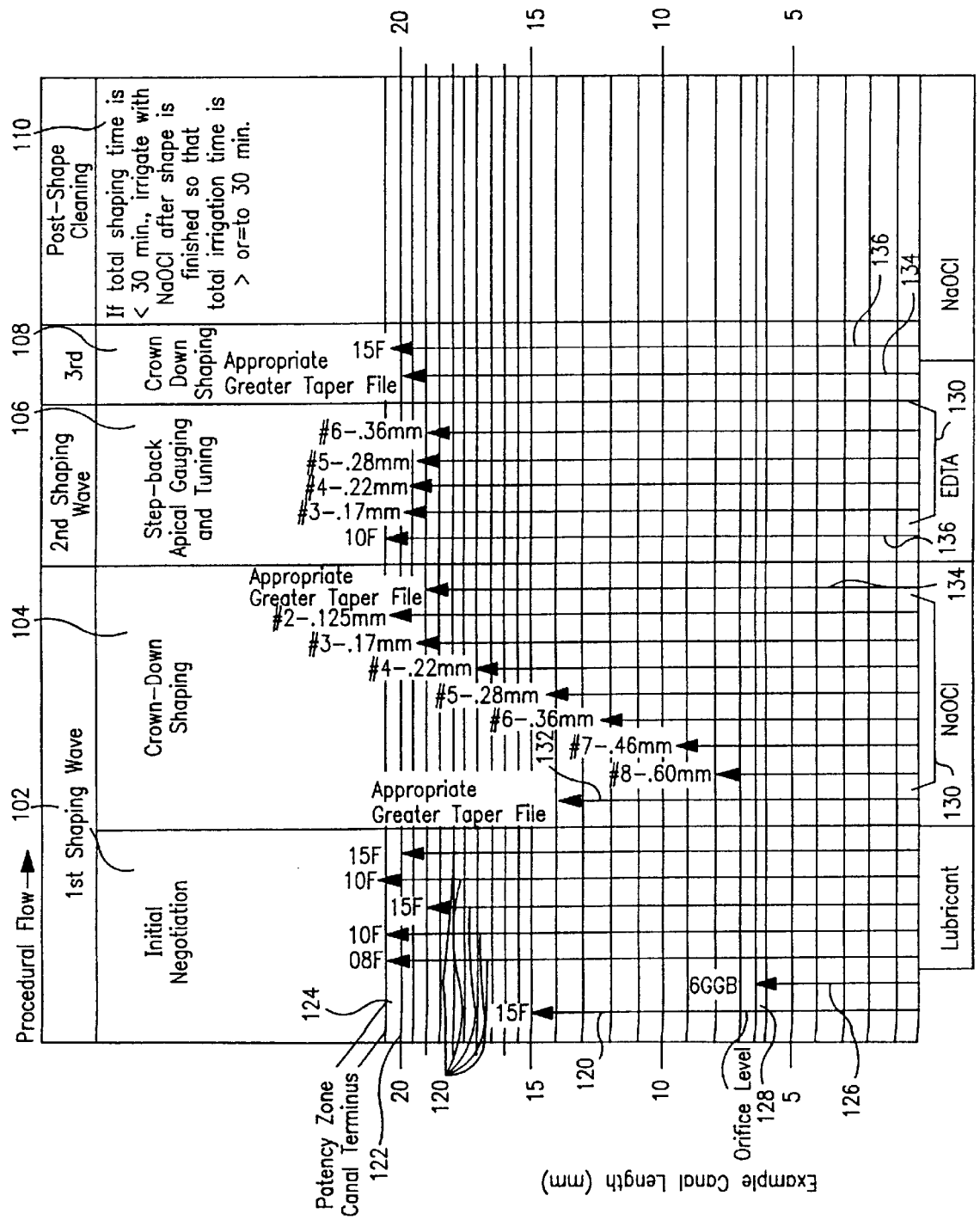
FIG. 3B is a flowchart illustrating further details of the method represented in FIG. 3A.

The flowchart of FIG. 3B illustrates the procedural flow, proceeding from left to right, of the three main steps 104, 106, 108 of the preferred method of the invention. This flowchart shows more particular details of the first, second and third shaping waves of the method of FIG. 3A and includes the initial negotiation step 102. In FIG. 3B, the initial negotiation step 102 is principally performed utilizing conventional K-files 120 in sizes from 08F to 15F, taking the negotiation files to the terminus of the root canal, in some instances past the canal terminus 122 into the patency zone 124 or beyond. Then a size 6 Gates-Glidden bur 126 is used at the orifice level 128 of canals to finish the access preparation and flare the orifice for easier introduction of instruments and materials to follow.

In the crown-down shaping step 104 following initial negotiation 102, a series of 0.04 taper ProFiles® 130 may be used, beginning with a No. 8 and proceeding to a No. 2 with penetration into different depths of the root as indicated. The No. 2 ProFile® is shown extending past the canal terminus 122 to the end of the patency zone 124. In this crown-down shaping step 104, if GT™ files are used, smaller ones 132 (0.06 or 0.08) would be selected for smaller roots, whereas larger ones 134 (0.10 or 0.12) would be selected for larger roots.

In the step-back apical gauging and tuning step 106 of the second shaping wave as indicated in FIG. 3B, a series of 0.04 taper ProFiles® 130 may be used in reverse order to the crown-down step 104, beginning with No. 3 and successively stepping back from the canal terminus through Nos. 4, 5 and 6. A 10F patency file 136 may also be used in conjunction with the ProFiles® 130 as the first file used in the step-back procedure in order to make sure the canal terminus is clear of debris which might be compacted by the other files.

In the second crown-down shaping step 108 of FIG. 3B, third shaping wave, an appropriate GT™ file 134 is used to extend the tapered preparation shape to the canal terminus.

Finally, the optional post-shape cleaning step 110 may follow the last crown-down shaping step 108, irrigating with NaOCl after the shape is finished in order that the total irrigation time is at least 30 minutes.

Figure 4:
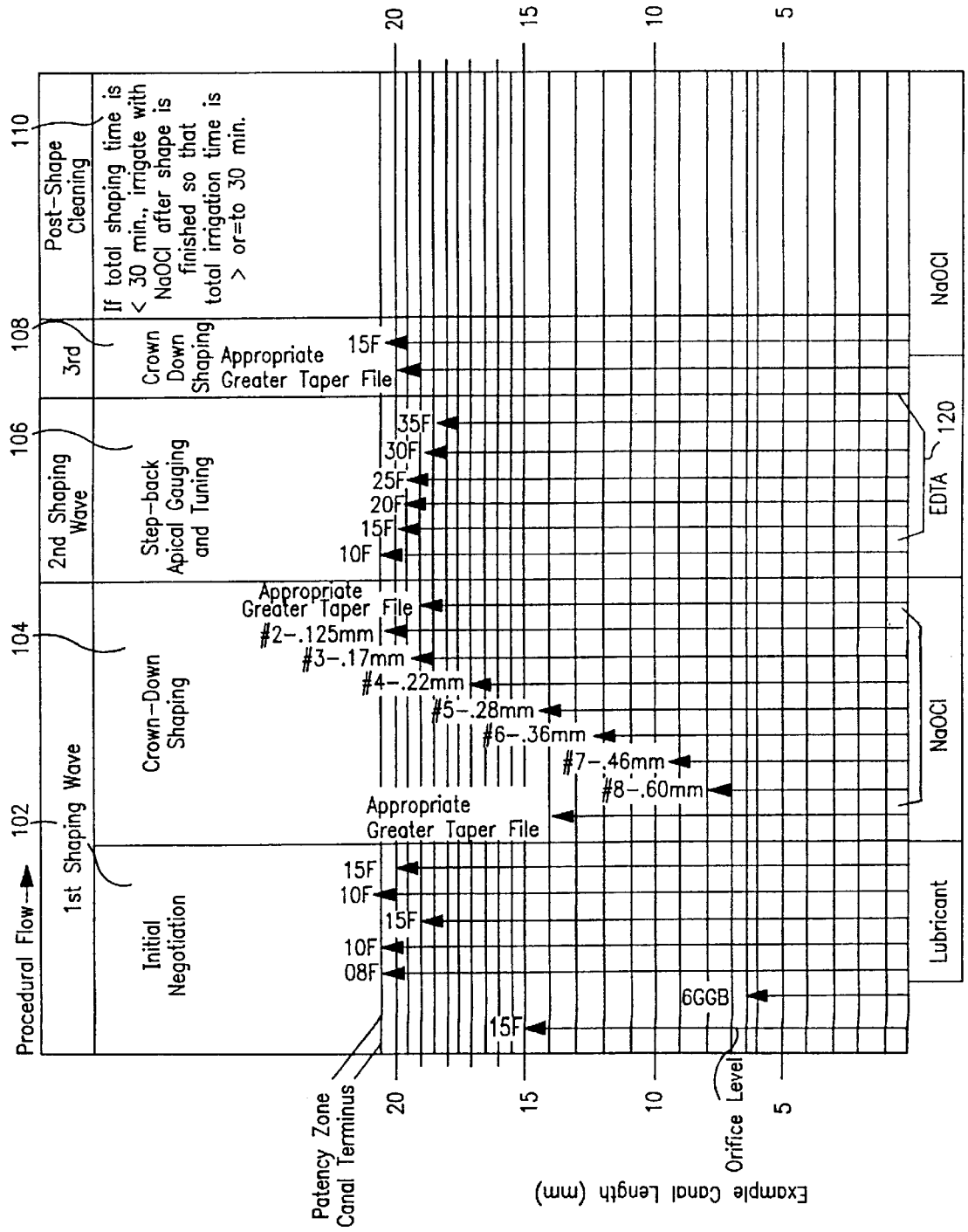
FIG. 4 is a flowchart representing particular details of a variant of the method of FIG. 3A in which the step-back is performed using a series of conventional K-files.

The flowchart of FIG. 4 is much the same as the flowchart of FIG. 3B, illustrating the crown-down/step-back/crown-down method of the invention with the exception that a series of conventional K-files 120 may be used in the step-back apical gauging and tuning step 106, second shaping wave, in place of the ProFiles® 130 shown in FIG. 3B. In FIG. 4, the K-files 120 used in the step-back step 106 proceed in succession from 15F through 20F, 25F, 30F and 35F with diminishing penetration of the files in negotiating the root canal in this step.

Figure 5:
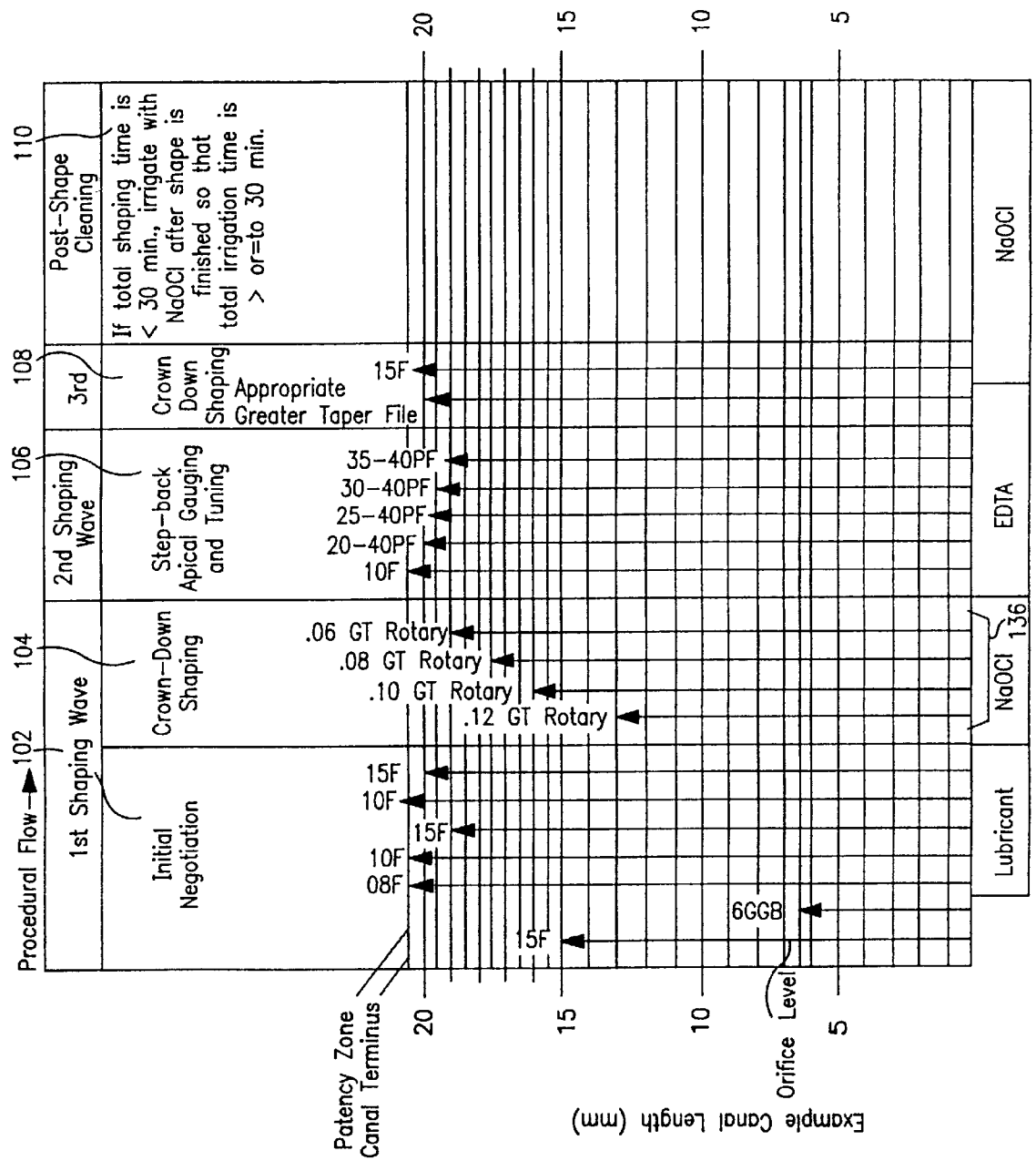
FIG. 5 is a flowchart illustrating another variant of the method of FIG. 3A in which still another series of files is utilized.

In the flowchart of FIG. 5 representing the method of the invention as a variant of FIG. 3A, the same series of files in the initial negotiation step 102 is used as listed in the chart of FIG. 3B. The crown-down shaping step 104 is the same as in FIG. 3B except that the ProFiles® 130 are replaced by greater taper rotary files 136, fewer in number. The apical gauging and tuning step 106 and the crown-down shaping step 108 in FIG. 5 are the same as in FIG. 3B.

Figure 6:
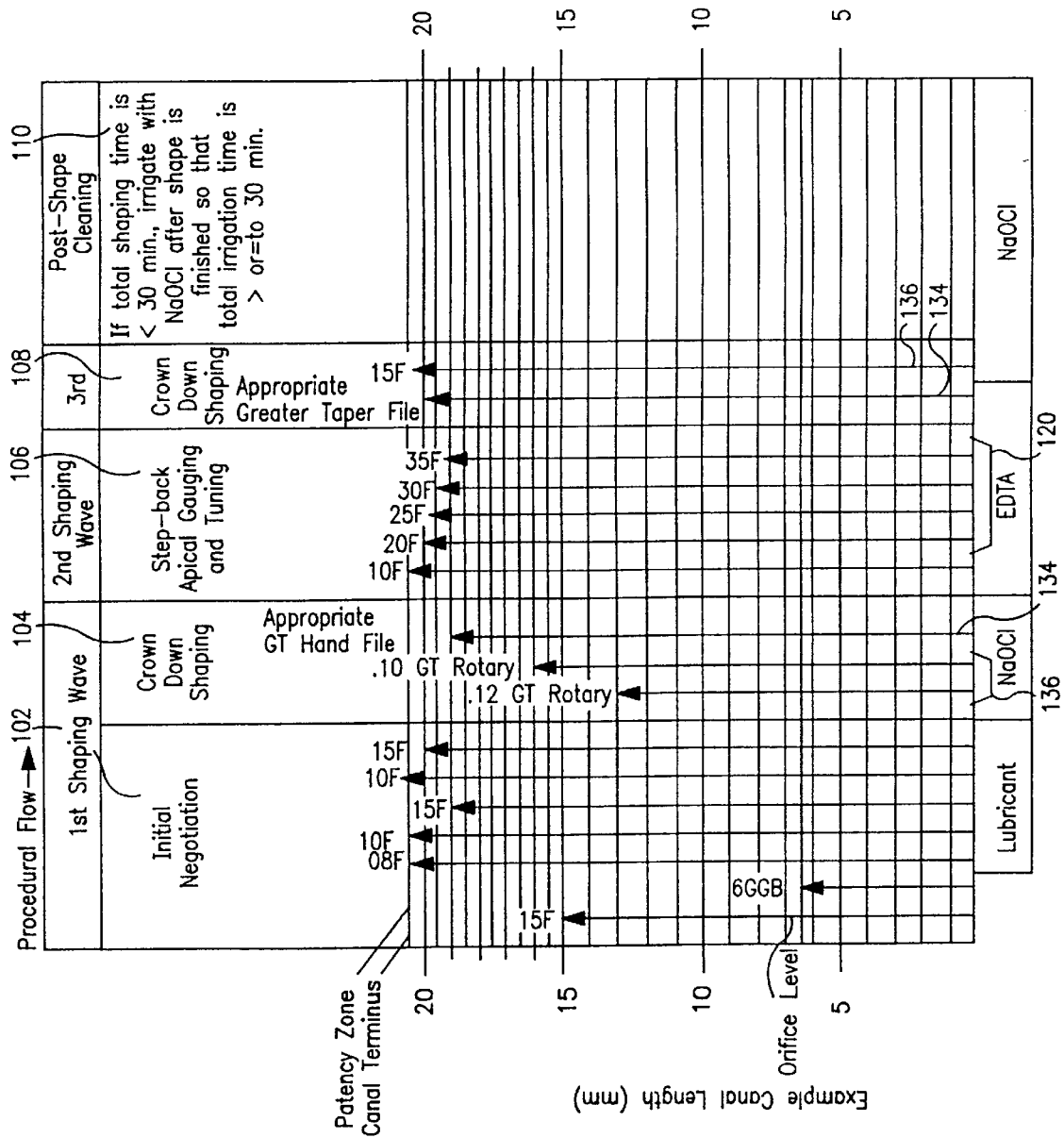
FIG. 6 is a flowchart illustrating still another variant of the method of FIG. 3A utilizing conventional K-files in the step-back step and a different series of files in the two crown-down steps of the method.

Finally, the flowchart of FIG. 6 shows the method of the invention as a variant of the method represented in FIG. 5 wherein the same series of files (conventional K-files) or Gates-Glidden burs is used in the initial negotiation step 102. The initial crown-down shaping step following initial negotiation in the first shaping wave is essentially the same also. The step-back apical gauging and tuning step 106 of the second shaping wave is also similar to that of the step 106 depicted in FIG. 5 except that a series of conventional K-files 120 is substituted for the ProFiles® 130 of FIG. 5. In the variant of the method represented in FIG. 6, an appropriate GT hand file 134 is used in place of the rotary file of the final crown-down step 108 of FIG. 5, along with the patency file No. 15F as indicated in FIG. 5. This technique is characterized by the use of hand files in the more curved apical regions of canals.

As shown and described in the above-discussed variations of the root canal preparation method of the invention, the present invention employs a series of files in a crown-down pre-enlargement subroutine to create ideal access to the fragile and often tortuous apical region of a canal. The tapered file is used to cut to a distance just short of the full root canal length. After the tapered file has been advanced to within approximately 1 to 2 mm of the root canal terminus, the tapered file is disengaged and the apical step back preparation is performed with optimal control owing to pre-enlargement of the first crown-down subroutine. The apical step-back procedure may be performed with any instrument series of choice; for example, a 0.02 or 0.04 tapered file series, used by hand manipulation or by handpiece power. The key factor in selection of instruments for this step-back subroutine is that they have less taper than the pre-enlarged canal shape.

After the apical step-back preparation is completed, the tapered file is again introduced to cut to the full length of the root canal. This is the second and final crown-down portion of the method. Practice of the disclosed methods of the invention provides a root canal having a pre-defined standardized taper extending all the way to the root canal terminus. Completion of the thus-prepared root canal with the pre-defined standardized taper is vastly simplified by using irrigation cannulas, condensation heat carriers and other instruments as well as paper points, gutta percha filling materials, and other auxiliary items, all having the same standardized taper.

Although there have been described hereinabove various specific arrangements of a ROOT CANAL PREPARATION METHOD in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A method of preparing a root canal in a tooth, which method comprises the steps of:
   a. Determining patency of a root canal system by performing an initial negotiation;
   b. Performing a first crown-down shaping procedure using a series of generally successively smaller files;
   c. Performing an apical step-back procedure using a series of generally successively larger files; and
   d. Performing a second crown-down shaping procedure using a series of generally successively smaller files in order to achieve consistent and desired shape of a treated root canal.

2. The method of claim 1, wherein said step of determining patency comprises inserting one or more fine instruments into a root canal for determining the extent and character of a root canal system.

3. The method of claim 1 wherein said step of determining patency further comprises removing all pulp fragments.

4. The method of claim 1 wherein said step of performing a first crown-down shaping procedure comprises using at least one of a series of greater taper files.

5. The method of claim 1 wherein said step of performing a first crown-down shaping procedure further comprises applying each file to cut to its own depth, without applying excessive force.

6. The method of claim 1 wherein said step of performing a first crown-down shaping procedure further comprises employing at least one tapered file in an engine-driven hand piece.

7. The method of claim 1 wherein said step of performing an apical step-back procedure further comprises selecting files having generally successively lesser tapers for insuring binding of the files primarily toward their tips.

8. The method of claim 1 wherein said step of performing an apical step-back procedure further comprises initiating the apical step-back procedure after determining that one of the files employed in the first crown-down shaping procedure has advanced to within several millimeters of the apical terminus of a root canal system.

9. The method of claim 1 wherein said step of performing a second crown-down shaping procedure comprises applying an appropriate shaping file for extending the root canal preparation to the root canal terminus whereby a consistent taper extending from the terminus to the coronal extent of the root canal preparation may be ensured.

10. A method of preparing a root canal in a tooth, which method comprises the steps of:
    a. Performing a first shaping wave by initially negotiating a root canal system and subsequently performing a first crown-down shaping procedure;
    b. Performing a second shaping wave by executing an apical step-back preparation; and
    c. Performing a third shaping wave by applying a second crown-down shaping procedure to achieve consistent and desired shape in the treated root canal.

11. A method of preparing a root canal in a tooth, said method comprising:
    a. Drilling through the crown of a tooth to provide access to the root;
    b. Selecting a patency implement from a set of patency implements;
    c. Using the selected patency implement to determine the distance to the terminus of the root canal;
    d. Selecting a shaping file from a set of shaping files;
    e. Using the selected shaping file to shape the root canal into a continuously tapering shape extending from the crown of the tooth down to within a relatively short distance of the root canal terminus;
    f. Selecting a tuning file from a set of tuning files;
    g. Using the selected tuning file to rough out the apical preparation and step back from the terminus of the continuously tapered root canal;
    h. Selecting a tapered file from a set of shaping files;
    i. Using the selected tapered file to shape the root canal into a continuously tapering shape extending from the tooth crown down to the root canal terminus;
    j. Irrigating the tapered root canal with an irrigating solution;
    k. Drying the tapered root canal with a drying means; and
    l. Inserting a sealing means to fill and seal the tapered root canal.

* * * * *